US00PP37180P2

(12) United States Plant Patent
Mukundan

(10) Patent No.: US PP37,180 P2
(45) Date of Patent: Dec. 30, 2025

(54) ***AGLAONEMA* PLANT NAMED 'MUKSTIL'**

(50) Latin Name: *Aglaonema hybrida*
Varietal Denomination: MUKSTIL

(71) Applicant: Parthasarathy Mukundan, Tamil Nadu (IN)

(72) Inventor: Parthasarathy Mukundan, Tamil Nadu (IN)

( * ) Notice: Subject to any disclaimer, the term of this patent is extended or adjusted under 35 U.S.C. 154(b) by 0 days.

(21) Appl. No.: 19/271,418

(22) Filed: Jul. 16, 2025

(51) Int. Cl.
*A01H 6/10* (2018.01)
*A01H 5/12* (2018.01)

(52) U.S. Cl.
USPC ..... Plt./376

(58) Field of Classification Search
USPC ..... Plt./376
CPC ..... A01H 6/10; A01H 5/12
See application file for complete search history.

*Primary Examiner* — Keith O. Robinson
(74) *Attorney, Agent, or Firm* — C. Anne Whealy

(57) ABSTRACT

A new and distinct cultivar of *Aglaonema* plant named 'MUKSTIL', characterized by its symmetrical and uniform shape; upright to slightly outwardly arching plant habit; relatively vigorous and robust growth habit with a large number of suckers produced; abundant sucker production and relatively short internodes gives a compact, dense and full plant form; upright, glossy and narrowly elliptic leaves with acuminate apices; leaves are dark green in color with a feather-patterned center that is silvery green in color; strong and flexible leaf petioles that are medium green in color; and relative tolerance to low production temperatures.

2 Drawing Sheets

Figure 1:
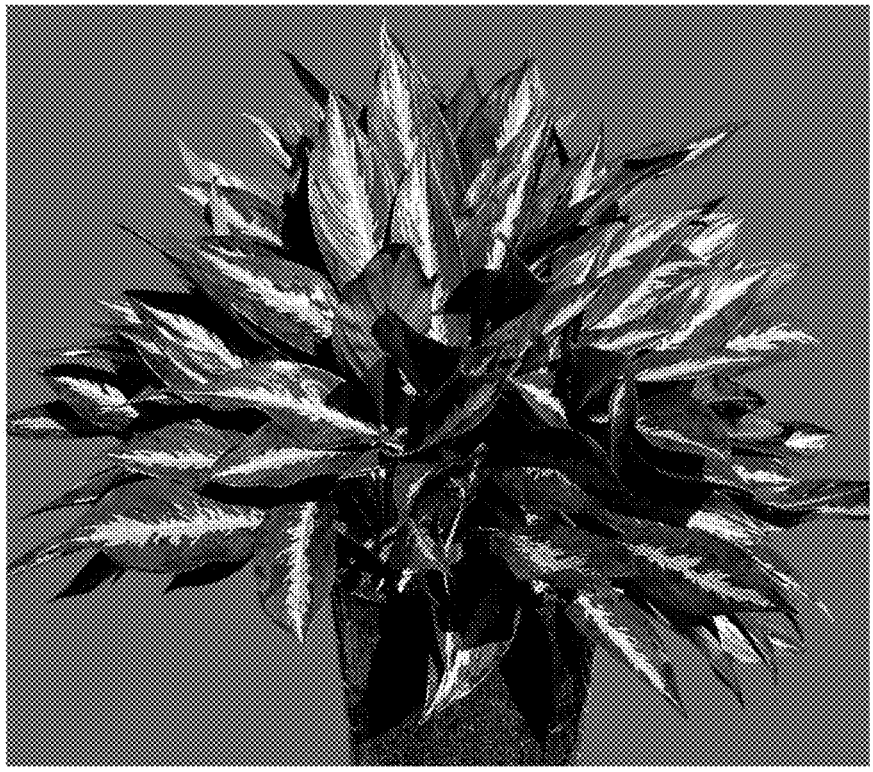

Botanical designation: *Aglaonema hybrida.*
Cultivar denomination: 'MUKSTIL'.

BACKGROUND OF THE INVENTION

The present invention relates to a new and distinct cultivar of *Aglaonema* plant, botanically known as *Aglaonema hybrida* and hereinafter referred to by the name 'MUKSTIL'.

The new *Aglaonema* plant is the product of a controlled breeding program conducted by the Inventor in Chamrajpet, Bangalore, India and Chennai, India. The objective of the breeding program is to create new compact and dense *Aglaonema* plants with good plant vigor, interesting and unique color and variegation patterns, resistance to pathogens and pests and tolerance to low temperatures.

The new *Aglaonema* plant is the product of a cross-pollination conducted by the Inventor on Jun. 24, 2007 in Chamrajpet, Bangalore, India of *Aglaonema hybrida* 'Gemini', not patented, as the female, or seed, parent with *Aglaonema hybrida* 'Silverado', disclosed in U.S. Plant Pat. No. 14,287, as the male, or pollen, parent. The new *Aglaonema* plant was discovered and selected by the Inventor on Mar. 3, 2008 as a single plant from within the resultant progeny of the stated cross-pollination in a controlled environment in Chennai, India.

Asexual reproduction of the new *Aglaonema* plant by cuttings and divisions in a controlled environment in Chennai, India since Jan. 15, 2009 has shown that the unique features of this new *Aglaonema* plant are stable and reproduced true to type in successive generations of asexual reproduction.

SUMMARY OF THE INVENTION

Plants of the new *Aglaonema* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'MUKSTIL'. These characteristics in combination distinguish 'MUKSTIL' as a new and distinct *Aglaonema* plant:

1. Symmetrical and uniform shape; upright to slightly outwardly arching plant habit.
2. Relatively vigorous and robust growth habit with a large number of suckers produced.
3. Abundant sucker production and relatively short internodes gives a compact, dense and full plant form.
4. Upright, glossy and narrowly elliptic leaves with acuminate apices; leaves are dark green in color with a feather-patterned center that is silvery green in color.
5. Strong and flexible leaf petioles that are medium green in color.
6. Relatively tolerant to low production temperatures.

Plants of the new *Aglaonema* differ primarily from plants of the female parent, 'Gemini', in the following characteristics:

1. Plants of the new *Aglaonema* are more symmetrically uniform than plants of 'Gemini'.
2. Plants of the new *Aglaonema* produce more suckers per plant and are denser and bushier than plants of 'Gemini'.
3. Leaves of plants of the new *Aglaonema* are shorter and narrower than leaves of 'Gemini'.
4. Leaves of plants of the new *Aglaonema* are not deformed whereas leaves of plants of 'Gemini' commonly exhibit leaf apex distortion.
5. Leaves of plants of the new *Aglaonema* are dark green in color with a feather-patterned center that is silvery green in color whereas leaves of plants of 'Gemini' are dark olive green in color with distinct silvery grey-colored chevrons in a lateral banded pattern.

Plants of the new *Aglaonema* differ primarily from plants of the male parent, 'Silverado', in the following characteristics:

1. Plants of the new *Aglaonema* are more symmetrically uniform than plants of 'Silverado'.
2. Plants of the new *Aglaonema* produce more suckers per plant and are denser and bushier than plants of 'Silverado'.
3. Leaves of plants of the new *Aglaonema* are held more upright than leaves of plants of 'Silverado'.
4. Leaves of plants of the new *Aglaonema* are shorter and narrower than leaves of 'Silverado'.
5. Leaves of plants of the new *Aglaonema* are not as undulate as leaves of plants of 'Silverado'.
6. Leaf petioles of plants of the new *Aglaonema* are darker green in color than leaf petioles of plants of 'Silverado'.

Plants of the new *Aglaonema* can be compared to plants of *Aglaonema hybrida* 'Mukgres', disclosed in U.S. Plant Pat. No. 23,971. In side-by-side comparisons, plants of the new *Aglaonema* differ primarily from plants of 'Mukgres', in the following characteristics:

1. Plants of the new *Aglaonema* are more symmetrically uniform than plants of 'Mukgres'.
2. Plants of the new *Aglaonema* can be grown in larger containers than plants of 'Mukgres'.
3. Leaves of plants of the new *Aglaonema* are held more upright than leaves of 'Mukgres'.
4. Leaves of plants of the new *Aglaonema* are broader than leaves of 'Mukgres'.
5. Leaves of plants of the new *Aglaonema* are dark green in color with a feather-patterned center that is silvery green in color whereas leaves of plants of 'Mukgres' have dark green-colored midvein, margins and irregular chevrons alternating with contrasting greyed green-colored irregular chevrons.

BRIEF DESCRIPTION OF THE PHOTOGRAPHS

The accompanying photographs illustrate the overall appearance of the new *Aglaonema* plant showing the colors as true as it is reasonably possible to obtain in colored reproductions of this type. Colors in the photographs may differ slightly from the color values cited in the detailed botanical description which accurately describe the colors of the new *Aglaonema* plant.

The photograph on the first sheet (FIG. 1) is a side perspective view of a typical plant of 'MUKSTIL' grown in a container.

Figure 2:
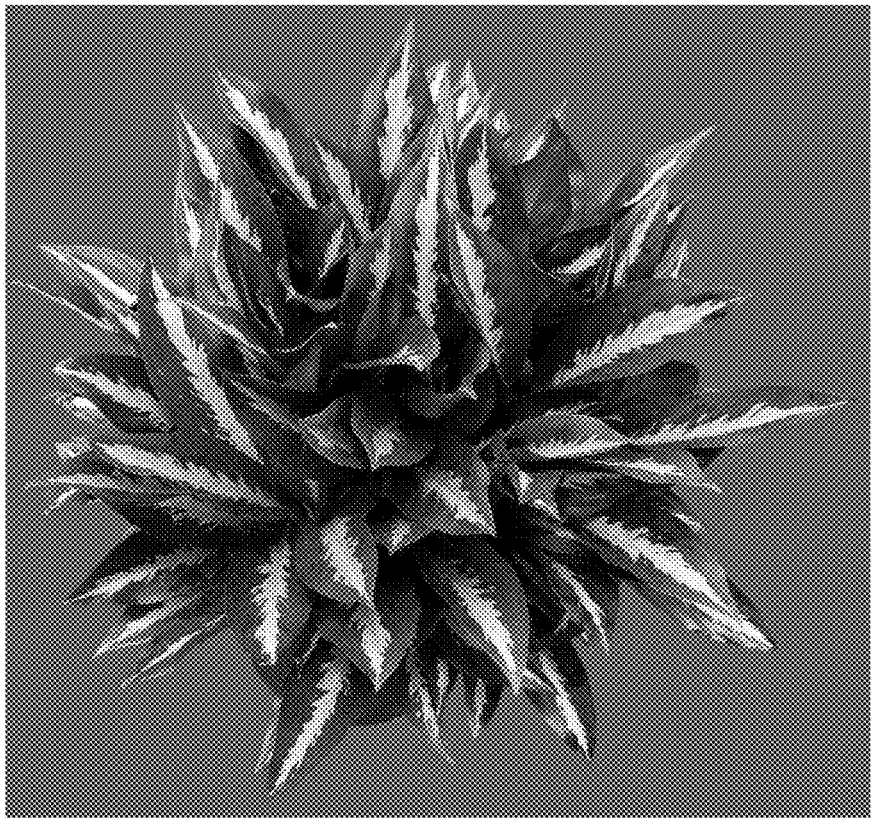

The photograph on the second sheet (FIG. 2) is a top perspective view of a typical plant of 'MUKSTIL' grown in a container.

DETAILED BOTANICAL DESCRIPTION

The aforementioned photographs and following observations and measurements describe plants grown in 15-cm containers during the early spring and summer in a polypropylene shade cloth-covered greenhouse in Miami, Florida. Plants were grown under environmental conditions and cultural practices which approximate those generally used in commercial *Aglaonema* production. During the production of the plants, temperatures ranged from 10° C. to 38° C. Plants were one year old when the photographs and the detailed description were taken. In the following description, color references are made to The Royal Horticultural Society Colour Chart, 2015 Edition, except where general terms of ordinary dictionary significance are used.

Botanical classification: *Aglaonema hybrida* 'MUKSTIL'.

Parentage:

*Female, or seed, parent.*—*Aglaonema hybrida* 'Gemini', not patented.

*Male, or pollen, parent.*—*Aglaonema hybrida* 'Silverado', disclosed in U.S. Plant Pat. No. 14,287.

Propagation:

*Type.*—By top cuttings, stem cuttings and divisions.

*Time to initiate roots, summer.*—About three to four weeks at temperatures about 25° C. to 32° C.

*Time to initiate roots, winter.*—About 30 to 40 days at temperatures about 12° C. to 25° C.

*Time to produce a rooted young plant, summer.*—About 30 to 35 days at temperatures about 25° C. to 32° C.

*Time to produce a rooted young plant roots, winter.*—About 45 to 60 days at temperatures about 12° C. to 25° C.

*Root description.*—Medium in thickness, fleshy; typically off-white in color, actual color of the roots dependent on substrate composition, water quality, fertilizer, substrate temperature and age of roots.

*Rooting habit.*—Freely branching; profusely dense.

Plant description:

*Plant and growth habit.*—Relatively compact; symmetrical and uniform shape; upright to slightly outwardly arching plant habit; relatively vigorous and robust growth habit with a large number of suckers produced; abundant sucker production and relatively short internodes gives a compact, dense and full plant form; leaves held mostly upright on strong petioles.

*Plant height, from soil level to top of leaf plane.*—About 57.5 cm.

*Plant diameter or spread.*—About 78.5 cm.

*Stem description.*—Aspect: Upright. Strength: Strong, sturdy; slightly flexible. Diameter, at the base: About 2.25 cm. Internode length, at the base: About 1 cm. Texture and luster: Smooth, glabrous; initially slightly glossy then becoming matte with development. Color: Developing: Close to 146A. Developed: Close to between 139A and 147A.

Leaf description:

*Arrangement.*—Whorled; simple.

*Length.*—About 32.5 cm.

*Width.*—About 11.5 cm.

*Shape.*—Narrowly elliptic.

*Apex.*—Acuminate.

*Base.*—Cuneate with attenuate tendencies.

*Margin.*—Entire; broadly undulate.

*Texture and luster, upper and lower surfaces.*—Smooth, glabrous; glossy.

*Venation pattern.*—Pinnate.

*Color.*—Developing leaves, upper surface: Ground color, close to between 146A and 146B; central feathered pattern color, close to 148C. Developing leaves, lower surface: Close to between 146A and 146B. Fully expanded leaves, upper surface: Ground color, close to between NN137A and N189A; central feathered pattern color, close to 191A to 191B;

venation, similar to lamina colors. Fully expanded leaves, lower surface: Close to 146A; venation, close to 146A.

*Petioles*.—Aspect: Mostly erect to slightly outwardly arching with development. Length: About 21.5 cm. Diameter, distally: About 7 mm by 8 mm. Diameter, proximally: About 2 cm by 2.2 cm. Strength: Strong, flexible; not brittle. Texture and luster: Smooth, glabrous; semi-glossy. Color: Outer surface: Close to 146A. Inner surface: Close to between 144A and 146A. Wing length: About 15.5 cm. Wing diameter, proximally: About 7.5 mm. Wing texture: Smooth, glabrous; towards the margin, membranous. Wing color: Outer surface: Close to 146A. Inner surface: Close to between 144A and 146A.

Inflorescence description: To date, inflorescence development has not been observed on plants of the new *Aglaonema*.

Pathogen & pest resistance: To date, plants of the new *Aglaonema* have not been observed to be resistant to pathogens or pests common to *Aglaonema*.

Temperature tolerance: Plants of the new *Aglaonema* have been observed to be relatively low temperature tolerant and to tolerate temperatures ranging from about 10° C. to about 38° C.

It is claimed:

1. A new and distinct *Aglaonema* plant named 'MUKSTIL' as herein illustrated and described.

* * * * *